United States Patent
De La Poterie et al.

(10) Patent No.: US 7,887,788 B2
(45) Date of Patent: *Feb. 15, 2011

(54) COSMETIC COMPOSITION COMPRISING A TACKY WAX

(75) Inventors: Valérie De La Poterie, Le Chatelet en Brie (FR); Thérèse Daubige, Mousseaux les Bray (FR); Patrice Styczen, Gif-sur-Yvette (FR)

(73) Assignee: L'Oreal S.A., Paris (FR)

( * ) Notice: Subject to any disclaimer, the term of this patent is extended or adjusted under 35 U.S.C. 154(b) by 1378 days.

This patent is subject to a terminal disclaimer.

(21) Appl. No.: 10/654,907

(22) Filed: Sep. 5, 2003

(65) Prior Publication Data

US 2004/0137021 A1    Jul. 15, 2004

Related U.S. Application Data

(60) Provisional application No. 60/418,345, filed on Oct. 16, 2002, provisional application No. 60/418,357, filed on Oct. 16, 2002, provisional application No. 60/412,853, filed on Sep. 24, 2002, provisional application No. 60/412,854, filed on Sep. 24, 2002, provisional application No. 60/412,855, filed on Sep. 24, 2002.

(30) Foreign Application Priority Data

| Sep. 6, 2002 | (FR) | 02 11096 |
| Sep. 6, 2002 | (FR) | 02 11097 |
| Sep. 6, 2002 | (FR) | 02 11104 |
| Sep. 30, 2002 | (FR) | 02 12097 |
| Sep. 30, 2002 | (FR) | 02 12098 |

(51) Int. Cl.
*A61Q 1/10* (2006.01)

(52) U.S. Cl. ..................... 424/70.7; 424/401

(58) Field of Classification Search ............ None
See application file for complete search history.

(56) References Cited

U.S. PATENT DOCUMENTS

| 3,673,160 A | 6/1972 | Buisson et al. |
| 3,802,841 A | 4/1974 | Robin |
| 3,937,811 A | 2/1976 | Papantoniou et al. |
| 4,887,622 A | 12/1989 | Gueret |
| 5,156,911 A | 10/1992 | Stewart |
| 5,159,052 A | 10/1992 | Barthelemy et al. |
| 5,356,627 A | 10/1994 | Da Cunha et al. |
| 5,429,816 A | 7/1995 | Hofrichter et al. |
| 5,472,798 A | 12/1995 | Kumazawa et al. |
| 5,519,063 A | 5/1996 | Mondet et al. |
| 5,591,424 A | 1/1997 | Hofrichter et al. |
| 5,650,144 A | 7/1997 | Hofrichter et al. |
| 5,736,125 A | 4/1998 | Morawsky et al. |
| 5,747,013 A | 5/1998 | Mougin et al. |
| 5,756,635 A | 5/1998 | Michaud et al. |
| 5,783,176 A | 7/1998 | Meiring et al. |
| 5,858,338 A | 1/1999 | Piot et al. |
| 5,860,432 A | 1/1999 | Gueret |
| 5,894,847 A | 4/1999 | Gueret |
| 5,925,337 A | 7/1999 | Arraudeau et al. |
| 5,934,292 A | 8/1999 | Gueret |
| 5,985,298 A | 11/1999 | Brieva et al. |
| 6,099,183 A | 8/2000 | Gueret |
| 6,103,221 A | 8/2000 | Arnaud et al. |
| 6,180,123 B1 | 1/2001 | Mondet |
| 6,214,329 B1 | 4/2001 | Brieva et al. |
| 6,227,735 B1 | 5/2001 | Gueret |
| 6,258,916 B1 | 7/2001 | Michaud et al. |
| 6,274,131 B1 | 8/2001 | Piot et al. |
| 6,345,923 B2 | 2/2002 | Gueret |
| 6,372,235 B1 | 4/2002 | Livoreil et al. |
| 6,464,967 B1 | 10/2002 | Collin |
| 6,491,927 B1 | 12/2002 | Arnaud et al. |
| 6,491,931 B1 | 12/2002 | Collin |
| 6,511,655 B1 | 1/2003 | Müller et al. |
| 6,875,245 B2 * | 4/2005 | Pavlin .................. 44/275 |

(Continued)

FOREIGN PATENT DOCUMENTS

DE    198 17 522    10/1999

(Continued)

OTHER PUBLICATIONS

Co-pending U.S. Appl. No. 10/654,887, filed Sep. 5, 2003.

(Continued)

*Primary Examiner*—Jyothsna A Venkat
(74) *Attorney, Agent, or Firm*—Finnegan, Henderson, Farabow, Garrett & Dunner, L.L.P.

(57) ABSTRACT

The disclosure herein relates to a cosmetic composition comprising at least 27% by weight of at least one wax having a tack of greater than or equal to 0.7 N·s and a hardness of less than or equal to 3.5 MPa.

The disclosure also relates to a cosmetic composition comprising at least one wax having a tack of greater than or equal to 0.7 N·s and a hardness of less than or equal to 3.5 MPa and a compound chosen from a dextrin ester of fatty acid(s) and/or a filler having a BET specific surface area of greater than or equal to 100 m²/g, and the disclosure further relates to an assembly (1) for packaging and applying a product for coating keratin fibers.

47 Claims, 1 Drawing Sheet

U.S. PATENT DOCUMENTS

| | | | |
|---|---|---|---|
| 7,288,262 | B1 | 10/2007 | Livoreil |
| 2002/0031533 | A1 | 3/2002 | Afriat |
| 2002/0098217 | A1 | 7/2002 | Piot et al. |
| 2002/0110571 | A1 | 8/2002 | Kanji et al. |
| 2002/0127257 | A1 | 9/2002 | Gers-Barlag et al. |
| 2002/0131941 | A1 | 9/2002 | Habeck et al. |
| 2003/0086951 | A9 | 5/2003 | Piot et al. |
| 2004/0071367 | A1 | 4/2004 | Irani et al. |
| 2004/0091447 | A1 | 5/2004 | Pays et al. |
| 2004/0096473 | A1 | 5/2004 | Jager-Lezer |
| 2004/0137020 | A1 | 7/2004 | De La Poterie et al. |
| 2004/0137021 | A1 | 7/2004 | De La Poterie et al. |
| 2004/0142831 | A1 | 7/2004 | Jager Lezer |
| 2005/0172421 | A1 | 8/2005 | Jager-Lezer et al. |
| 2005/0188474 | A1 | 9/2005 | De La Poterie et al. |
| 2005/0191258 | A1 | 9/2005 | De La Poterie et al. |
| 2005/0191262 | A1 | 9/2005 | De La Poterie et al. |

FOREIGN PATENT DOCUMENTS

| | | |
|---|---|---|
| EP | 0 360 708 | 3/1990 |
| EP | 0 549 494 | 6/1993 |
| EP | 0 686 858 | 12/1995 |
| EP | 0 951 897 | 10/1999 |
| EP | 0 955 039 | 11/1999 |
| EP | 0 998 905 B1 | 5/2000 |
| EP | 1 068 854 | 1/2001 |
| EP | 1 080 713 A2 | 3/2001 |
| EP | 1 086 945 | 3/2001 |
| EP | 1 157 683 | 11/2001 |
| EP | 1 172 078 | 1/2002 |
| EP | 1 191 041 | 3/2002 |
| EP | 1 201 221 | 5/2002 |
| EP | 0 921 217 | 12/2003 |
| EP | 1 396 257 | 3/2004 |
| EP | 1 396 258 | 3/2004 |
| EP | 1 396 259 | 3/2004 |
| EP | 1 400 234 | 3/2004 |
| EP | 1 424 058 | 6/2004 |
| FR | 2 079 785 | 11/1971 |
| FR | 2 687 569 | 8/1993 |
| FR | 2 773 063 | 7/1999 |
| FR | 2 792 190 | 10/2000 |
| FR | 2 844 185 | 3/2004 |
| FR | 2 844 710 | 3/2004 |
| FR | 2 844 999 | 4/2004 |
| JP | H06-9341 | 1/1994 |
| JP | H08-506342 | 7/1996 |
| JP | H09-132511 | 5/1997 |
| JP | H11-255619 | 9/1999 |
| JP | 2000-136110 | 5/2000 |
| JP | 2001-48750 | 2/2001 |
| JP | 2001-64156 | 3/2001 |
| JP | 2002-145739 | 5/2002 |
| JP | 2003-95873 | 4/2003 |
| JP | 2003-95875 | 4/2003 |
| WO | WO 93/23008 | 11/1993 |
| WO | WO 94/17775 | 8/1994 |
| WO | WO 98/42298 | 10/1998 |
| WO | WO 01/03653 | 1/2001 |
| WO | WO 01/19333 | 3/2001 |
| WO | WO 02/03931 | 1/2002 |
| WO | WO 02/47031 | 6/2002 |

OTHER PUBLICATIONS

French Search Report for FR 0211104 (French priority application for co-pending U.S. Appl. No. 10/654,887), dated Apr. 28, 2003.
English language Derwent Abstract for EP 1 080 713 A2.
English language Derwent Abstract for JP H06-9341.
English language Derwent Abstract for JP H09-132511.
French Search Report, dated May 19, 2003.
Encyclopedia of Chemical Technology, "Sulfonation and Sulfation to Thorium and Thorium Compounds", Third Edition, vol. 22, 1993, p. 333-432.
English language Derwent Abstract for DE 197 51 221, May 1999.
WO 91/12793 (Sep. 5, 1991) Abstract.
Office Action dated Apr. 1, 2008 in co-pending U.S. Appl. No. 10/654,887, filed Sep. 5, 2003.
Co-pending U.S. Appl. No. 10/654,887, filed Sep. 5, 2003.
French Search Report for FR 0211104 (French priority application for co-pending U.S. Appl. No. 10/654,887), dated Apr. 28, 2003.
English language Derwent Abstract for EP 1 080 713 A2, Mar. 7, 2001.
English language Derwent Abstract for JP H06-9341, Jan. 18, 1994.
English language Derwent Abstract for JP H09-132511, May 20, 1997.
English language Derwent Abstract for JP 2003-95873, Apr. 3, 2003.
English language Derwent Abstract of JP 2003-95875, Apr. 3, 2003.
Abstract for Okuyama, M. "Recent Research and Development of Mascara and Eyeliner," Fragrance Journal, 1997, vol. 25, No. 8, pp. 58-64.
Boutevin, B. et al., "Study of Morphological and Mechanical Properties of PP/PBT," Polymer Bulletin, 34, pp. 117-123, (1995).
Co-pending Application No. 10/656,201, filed Sep. 8, 2003.
Co-pending U.S. Appl. No. 11/056,239, filed Feb. 14, 2005.
English language Abstract of EP 1 172 078, dated Jan. 16, 2002.
English language Abstract of FR 2 079 785, dated Nov. 12, 1971.
English language Abstract of FR 2 792 190, dated Oct. 20, 2000.
English language Abstract of FR 2 844 710, dated Mar. 26, 2004.
English language Abstract of FR 2 844 999, dated Apr. 2, 2004.
English translation of Notice of Reasons for Rejection mailed May 29, 2007, in the related Japanese Patent Application No. 2005-33677.
European Search Report No. EP 05 29 0253, dated Apr. 28, 2005.
Hamley, I.W., "Crystallization in Block Copolymers," Advances in Polymer Science, vol. 148, pp. 113-137 (1999).
Nojima, S. et al., "Melting Behavior of Poly (e-caprolactone)-block-Polybutadiene Copolymers," Macromolecules, vol. 32, No. 11, pp. 3727-3734 (1999).
Notice of Allowance mailed in co-pending U.S. Appl. No. 11/056,239, dated Jun. 16, 2010.
Office Action mailed Apr. 29, 2009, in co-pending U.S. Appl. No. 11/056,239.
Office Action mailed Aug. 18, 2009, in co-pending U.S. Appl. No. 10/654,887.
Office Action mailed Aug. 28, 2007, in co-pending U.S. Appl. No. 10/656,201.
Office Action mailed Dec. 11, 2009, in co-pending U.S. Appl. No. 11/056,239.
Office Action mailed Feb. 10, 2009, in co-pending U.S. Appl. No. 10/656,201.
Office Action mailed Mar. 31, 2010, in co-pending U.S. Appl. No. 10/656,201.
Office Action mailed May 30, 2008, in co-pending U.S. Appl. No. 10/656,201.
Okuyama, M. "Recent Research and Development of Mascara and Eyeliner," Fragrance Journal, 1997, vol. 25, No. 8, pp. 58-64.
Pigeon, R. et al., "Chimie Macromoléculaire Appliquée," vol. 40/41, No. 600, pp. 139-158 (1974).
Prince, L.M., "Microemulsions Theory and Practice," Academic Press, 1977, pp. 21-32.
Rangarajan P., et al., "Morphology of Semi-Crystalline Block Copolymers of Ethylene-(ethylene-alt-propylene)," Macromolecules, 26, 4640-4645 (1993).
Richter, P. et al., "Polymer Aggregates with Crystalline Cores: The System Poly(ethylene)-poly(ethylene-propylene)," Macromolecules, 30, 1053-1068 (1997).
Summary of Pigeon, R. et al., "Chimie Macromoléculaire Appliquée, ", vol. 40/41, No. 600, pp. 139-158 (1974).
Terech, P., "Low-Molecular Weight Organogelators," Specialist Surfactants, Chapter 8, 1997, pp. 209-263.

* cited by examiner

COSMETIC COMPOSITION COMPRISING A TACKY WAX

This application claims benefit of U.S. Provisional Application No. 60/412,853, filed Sep. 24, 2002; U.S. Provisional Application No. 60/418,345, filed Oct. 16, 2002; U.S. Provisional Application No. 60/418,357, filed Oct. 16, 2002; U.S. Provisional Application No. 60/412,854, filed Sep. 24, 2002; and U.S. Provisional Application No. 60/412,855, filed Sep. 24, 2002. This application also claims benefit of priority under 35 U.S.C. §119 to French Patent Application No. 02 11096, filed Sep. 6, 2002; French Patent Application No. 02 11104, filed Sep. 6, 2002; French Patent Application No. 02 11097, filed Sep. 6, 2002; French Patent Application No. 02 12097, filed Sep. 30, 2002; and French Patent Application No. 02 12098, filed Sep. 30, 2002.

Disclosed herein is a cosmetic composition comprising at least one tacky wax. This composition may be used, for example, in the field of makeup or care of human keratin materials such as the skin, the nails, the eyelashes, the eyebrows and the hair. Also disclosed herein is a cosmetic care or makeup process for keratin materials.

The cosmetic composition may be in the form of a product for coating keratin fibres such as the eyebrows, the hair or the eyelashes, or may be in the form of an eyeliner, an eye shadow, a makeup rouge, a foundation, a lip product or a body makeup product (for instance, a semi-permanent tattoo). Further disclosed herein is a care or makeup composition for keratin fibres, for example, a care or makeup composition for the eyebrows or eyelashes.

The cosmetic composition, when it is in a form for coating keratin fibres, may be a makeup composition, a composition to be applied onto a makeup, also known as a top coat, or a treating (or care) composition for the eyelashes, the eyebrows or the hair.

Mascaras are commonly prepared according to two types of formulations: water-based mascaras, known as cream mascaras, in the form of an emulsion of waxes in water; and anhydrous mascaras or mascaras with a low water content, known as waterproof mascaras, in the form of dispersions of waxes in organic solvents.

It is known practice to use various waxes to formulate mascaras, for instance those described in document WO-A-91/12793, for example beeswax, candelilla wax, carnauba wax or polyethylene wax.

However, when mascaras comprise certain waxes (for instance, carnauba wax, rice bran wax or polyethylene wax) in a large amount (i.e., above 20% by weight relative to the total weight of the mascara), the deposit of the eyelash makeup obtained can look grainy, which may result in a non-smooth and non-uniform makeup result, these defects rendering the makeup result unattractive.

Moreover, to obtain a mascara with good charging properties, i.e., to obtain heavy makeup for eyelashes, it is possible to incorporate into the mascara one or more waxes in a total amount of greater than 25% by weight relative to the total weight of the mascara. However, when using conventional waxes such as beeswax, candelilla wax or carnauba wax at these amounts, the mascara composition can acquire a very thick consistency, or even become too compact, and may not be applied easily to the eyelashes with the mascara brush applicators commonly used. The excessively thick mascara deposited on the eyelashes may be in the form of lumps and the makeup result thus obtained may not have the desired smooth appearance, such that the makeup result is not uniform and looks unattractive.

In addition, certain waxes such as orange wax or lanolin wax, used at concentrations of greater than 25% by weight, relative to the total weight of the composition, produce compositions that may not be sufficiently stable, for example, after storage for two weeks at room temperature (25° C.), the composition can set to a solid (substantial increase in viscosity) or undergo a phase separation that may be seen with the naked eye.

Also disclosed herein is a makeup or care composition for keratin materials comprising a high wax content, making it possible to obtain a smooth, uniform deposit on keratin materials.

Further disclosed herein is a cosmetic composition that may be applied easily to keratin materials, in a form that makes it possible to obtain rapidly the expected cosmetic composition, e.g., makeup, and that may comprise a high content of wax.

Still further disclosed herein is a cosmetic composition comprising a high content of wax, which can remain stable, for example, after storage for 24 hours at 25° C., or, for further example, for 15 days.

It has been discovered that such a composition may be obtained by using a particular wax that has tacky properties (high tack). Such a wax can produce a cosmetic composition that applies easily to keratin materials, shows good attachment to keratin materials, that make it possible to obtain rapidly the expected makeup, and leads to the formation of a smooth, uniform makeup result that does not look grainy.

Furthermore, the tacky wax may be incorporated into the composition in a concentration of up to 60% by weight, relative to the total weight of the composition, without the composition setting to a solid. In addition, compositions comprising the tacky wax are stable (such as, in terms of stability after 24 hours at 25° C.), retain a creamy consistency, and apply easily to keratin materials.

More specifically, an embodiment disclosed herein is a makeup or care composition for keratin materials comprising, in a cosmetically acceptable medium, at least one wax in an amount of at least 27% by weight, relative to the total weight of the composition, said wax having a tack of greater than or equal to 0.7 N·s and a hardness of less than or equal to 3.5 MPa.

Also disclosed herein is a non-therapeutic cosmetic makeup or care process for keratin materials, for instance, the skin, the nails, the hair, the eyelashes and the eyebrows, comprising the application to keratin materials of a composition as defined above.

Also disclosed herein is the use of a composition as defined above to obtain a uniform and/or smooth and/or rapidly obtained makeup result on keratin materials.

Also disclosed herein is the use of at least one wax having a tack of greater than or equal to 0.7 N·s and a hardness of less than or equal to 3.5 MPa, in a cosmetic composition, to obtain a uniform and/or smooth makeup result on keratin materials and/or to obtain a stable cosmetic composition, wherein the at least one wax is present in a concentration of at least 27% by weight, relative to the total weight of the composition.

For certain cosmetic applications, it can be advantageous to be able to moderate the natural tack of the tacky wax while at the same time maintaining the advantageous smooth, uniform deposit properties. In the case of formulations of mascara, certain users wish to obtain a perfect individualization of the eyelashes, which is not always optimum in the presence of a tacky wax.

The inventors have found, unexpectedly, that it is possible to satisfy this additional requirement provided that the said tacky wax is combined with at least one compound chosen from dextrin esters of fatty acids and fillers with a BET specific surface area of greater than or equal to 100 m²/g.

Accordingly, disclosed herein is a cosmetic composition comprising, in a cosmetically acceptable medium, at least one wax having a tack of greater than or equal to 0.7 N·s and a hardness of less than or equal to 3.5 MPa and at least one compound chosen from dextrin esters of fatty acids and/or fillers with a BET specific surface area of greater than or equal to 100 m²/g.

Also disclosed herein is a non-therapeutic cosmetic makeup or care process for keratin materials, for example, the skin, the nails, the hair, the eyelashes and the eyebrows, comprising applying to the keratin materials the composition as defined above.

Also disclosed herein is the use of the composition as defined above to produce a uniform and/or smooth makeup result on keratin materials, for instance, a charging and separating makeup result on the eyelashes.

Also disclosed herein is the use of at least one compound chosen from dextrin esters of fatty acids and fillers with a BET specific surface area of greater than or equal to 100 m²/g, in a cosmetic composition comprising a wax having a tack of greater than or equal to 0.7 N·s and a hardness of less than or equal to 3.5 Mpa, to obtain a uniform and/or smooth makeup result on keratin materials, for example a charging and separating makeup result on keratin fibres, and/or to obtain a stable cosmetic composition, the wax being present in an amount of at least 10%, for example, at least 20% and for further example, at least 25%, by weight relative to the total weight of the composition.

The term "cosmetically acceptable medium" means a cosmetic medium that is compatible with keratin materials such as the skin, including the lips, the nails, the hair, the eyelashes and the eyebrows.

TACKY WAX

Figure 1:
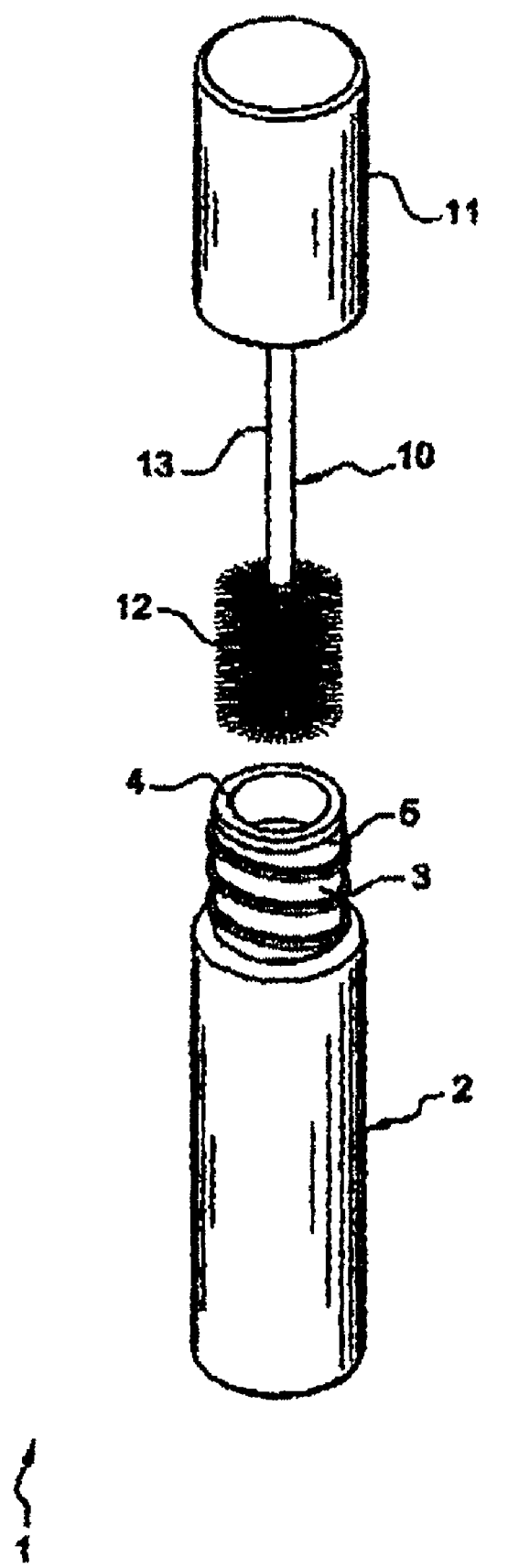
FIG. 1 shows a packaging and applicator assembly containing a mascara composition according to the present disclosure.

The at least one wax, also known as a tacky wax, present in the composition as disclosed herein has a tack of greater than or equal to 0.7 N·s, for example ranging from 0.7 N·s to 30 N·s, such as a tack greater than or equal to 1 N·s, for further example ranging from 1 N·s to 20 N·s such as a tack greater than or equal to 2 N·s, and for even further example, ranging from 2 N·s to 10 N·s, for instance ranging from 2 N·s to 5 N·s.

The at least one tacky wax has a hardness of less than or equal to 3.5 MPa, for example, ranging from 0.01 to 3.5 MPa, and for further example, ranging from 0.05 MPa to 3 MPa, for instance, ranging from 0.1 MPa to 2.5 MPa.

For the purposes of the present disclosure, the term "wax" means a lipophilic fatty compound that is solid at room temperature (25° C.) and atmospheric pressure (760 mm Hg, i.e. $10^5$ Pa), with a reversible solid/liquid change of state, having a melting point of greater than 30° C., for example, greater than 55° C., which may be up to 200° C., for instance, up to 120° C.

By bringing the wax to its melting point, it is possible to make it miscible with oils and to form a microscopically homogeneous mixture, but on cooling the mixture to room temperature, recrystallization of the wax in the oils of the mixture is obtained.

The melting point values correspond, as disclosed herein, to the melting peak measured using a differential scanning calorimeter (D.S.C.), for example the calorimeter sold under the name DSC 30 by the company Mettler, with a temperature rise of 5 or 10° C. per minute.

The tack of the at least one wax is measured at 20° C. using the texturometer sold under the name TA-XT2i by the company Rheo, equipped with an acrylic polymer rotor in the form of a cone forming an angle of 45°, by measuring the change in force (compression force or stretching force) (F) as a function of time, during the following operation: The rotor is displaced at a speed of 0.5 mm/s and then penetrates into the wax to a penetration depth of 2 mm. When the rotor has penetrated the wax to a depth of 2 mm, the rotor is held stationary for 1 second (corresponding to the relaxation time) and is then withdrawn at a speed of 0.5 mm/s. During the relaxation time, the force (compression force) decreases greatly until it becomes zero, and then, during the withdrawal of the rotor, the force (stretching force) becomes negative before rising again to the value 0. Tack corresponds to the integral of the curve of the force as a function of time for the portion of the curve corresponding to the negative force values (stretching force). The tack value is expressed in N·s.

To perform the tack measurement of the wax, the wax is melted at a temperature equal to the melting point of the wax +10° C. The molten wax is cast in a container 25 mm in diameter and 20 mm deep. The wax is recrystallized at room temperature (25° C.) for 24 hours such that the surface of the wax is flat and smooth, and the wax is then kept for at least 1 hour at 20° C. before performing the tack measurement.

The hardness of the at least one wax is determined by measuring the maximum compression force, which is measured at 20° C. using the texturometer sold under the name TA-XT2i by the company Rheo, equipped with a stainless-steel cylinder 2 mm in diameter travelling at a measuring speed of 0.1 mm/s, and penetrating the wax to a penetration depth of 0.3 mm. To perform the hardness measurement, the wax is melted at a temperature equal to the melting point of the wax +20° C. The molten wax is cast in a container 30 mm in diameter and 20 mm deep. The wax is recrystallized at room temperature (25° C.) for 24 hours and is then kept for at least 1 hour at 20° C. before performing the hardness measurement. The hardness value is the compression force measured divided by the area of the texturometer cylinder in contact with the wax.

Tacky waxes that may be used include the $C_{20}$-$C_{40}$ alkyl (hydroxystearoyloxy)stearates (the alkyl group comprising from 20 to 40 carbon atoms). For example, the tacky wax that may be used comprises at least one $C_{20}$-$C_{40}$ alkyl 12-(12'-hydroxystearoyloxy)stearate of formula (I):

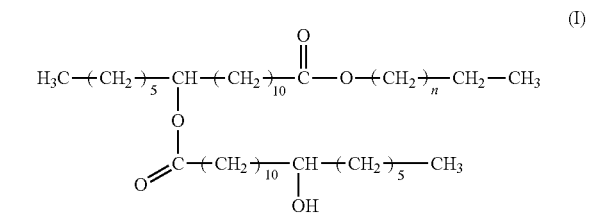

wherein n is an integer ranging from 18 to 38.

Thus, disclosed herein is a makeup or care composition for keratin materials comprising, in a cosmetically acceptable medium, at least one $C_{20}$-$C_{40}$ alkyl (hydroxystearoyloxy)s- tearate (for instance, a $C_{20}$-$C_{40}$ alkyl 12-(12'-hydroxystearoyloxy)stearate), for example as disclosed in formula (I) above.

Such at least one wax is sold under the names "Kester Wax K 82 P" and "Kester Wax K 80 P" by the company Koster Keunen.

The at least one wax may be in the form of an aqueous microdispersion of wax particles. The expression "aqueous microdispersion of wax" as disclosed herein means an aqueous dispersion of wax particles in which the size of the said wax particles is less than or equal to about 1 µm. Wax microdispersions are stable dispersions of colloidal wax particles, and are described especially in "Microemulsions Theory and Practice", L. M. Prince Ed., Academic Press (1977) pages 21-32.

These wax microdispersions may be obtained by melting the wax in the presence of a surfactant, and optionally in a portion of water, followed by gradual addition of hot water with stirring. The intermediate formation of an emulsion of the water-in-oil type is observed, followed by a phase inversion, with final production of a microemulsion of the oil-in-water type. On cooling, a stable microdispersion of solid wax colloidal particles is obtained. The wax microdispersions may also be obtained by stirring the mixture of wax, surfactant and water using stirring means such as ultrasound, a high-pressure homogenizer, or turbomixers.

The particles of the wax microdispersion can have mean sizes of less than 1 µm (for instance ranging from 0.02 µm to 0.99 µm), for example, less than 0.5 µm (for instance ranging from 0.06 µm to 0.5 µm). These particles are mainly comprised of a wax or a mixture of waxes. However, they may comprise a small proportion of oily and/or pasty fatty additives, a surfactant and/or a common liposoluble additive/active agent.

The at least one wax or tacky wax may be present in the composition according to the invention in an amount ranging from 0.5% to 60% by weight, for example, from 1% to 50% by weight and for further example, ranging from 10% to 40% by weight, relative to the total weight of the composition.

The at least one tacky wax may be present in the composition as disclosed herein in an amount greater than 27% by weight relative to the total weight of the composition, for example ranging from 27% to 60% by weight, such as greater than 28% by weight, for further example from 28% to 50% by weight, such as greater than 30% by weight, for instance from 30% to 40% by weight.

Additional Wax

Advantageously, the composition as disclosed herein comprises at least one additional wax, also known as the hard wax, which has a hardness of greater than or equal to 6 MPa, for example, ranging from 6 MPa to 30 MPa, such as greater than or equal to 7 MPa, for further example, ranging from 7 MPa to 25 MPa, such as greater than or equal to 8 MPa, for even further example, ranging from 8 to 25 MPa, such as greater than or equal to 9 MPa, and for still further example ranging from 9 to 20 MPa. The hardness of the hard wax is measured according to the same protocol described above for the first (e.g., tacky) wax.

Hard waxes that may be used include, by way of non-limiting example, carnauba wax, candelilla wax, polyethylene waxes, hydrogenated jojoba oil, sumach wax, ceresin, octacosanyl stearate, tetracontanyl stearate, shellac wax, behenyl fumarate, bis(1,1,1-trimethylolpropane) tetrastearate sold under the name "Hest 2T-4S" by the company Heterene, bis(1,1,1-trimethylolpropane) tetrabehenate sold under the name Hest 2T-4B by the company Heterene, ozokerites, for instance the product sold under the name "Ozokerite Wax SP 1020 P" by the company Strahl & Pitsch, and the wax obtained by hydrogenation of olive oil esterified with stearyl alcohol, sold under the name Phytowax Olive 18 L 57 by the company Sophim.

The at least one additional wax (e.g. hard wax), may be in the form of an aqueous microdispersion of wax particles, as described for the at least one tacky wax.

The at least one additional wax, or hard wax, may be present in the composition as disclosed herein, in an amount ranging from 0.1% to 30% by weight, for instance ranging from 1% to 20% by weight and for further instance ranging from 2% to 10% by weight, relative to the total weight of the composition.

As disclosed herein, when the tack needs to be adjusted, it is advantageous to combine the at least one tacky wax with a compound chosen from dextrin esters of fatty acids and/or fillers having a BET specific surface area of greater than or equal to 100 $m^2/g$.

Filler with a Specific Surface Area

The filler may have a specific surface area of greater than or equal to 100 $m^2/g$, for example, ranging from 100 to 5000 $m^2/g$, such as from 150 to 1000 $m^2/g$, or for further example, from 200 to 800 $m^2/g$.

The term "filler" as described herein denotes particles of any shape, which are insoluble in the medium of the composition, irrespective of the temperature at which the composition is manufactured.

The expression "filler with a specific surface area" as disclosed herein means a filler having a specific surface area measured according to the BET method of greater than or equal to 100 $m^2/g$.

The "BET specific surface area" is determined according to the BET (Brunauer-Emmet-Teller) method described in "The Journal of the American Chemical Society", vol. 60, page 309, February 1938, and corresponding to international standard ISO 5794/1 (appendix D). The BET specific surface area corresponds to the total specific surface area (i.e. micropores included) of the filler.

The amount of filler in the composition according to the disclosure is generally adjusted so as to control the tack of the combined wax to the desired value. Thus, the fillers as disclosed herein can be useful for preparing cosmetic compositions comprising at least 10%, for example, 20%, and for further example, at least 25% and for still further example, 27% by weight of the at least one tacky wax.

By way of illustration, this filler may be present in the composition according to an embodiment as disclosed herein, in an amount ranging from 0.1% to 25%, such as from 0.5% to 20% and for instance from 1% to 15% by weight, relative to the total weight of the composition.

The at least one tacky wax and the filler with a specific surface area can be present in an amount such that the weight ratio of the tacky wax relative to the filler with a specific surface area ranges from 350 to 0.1, such as from 100 to 0.5, for example, from 50 to 0.8 and for further example, from 30 to 1.

The particles of which the filler with a specific surface area is composed may have a mean size ranging from 0.01 to 100 µm, such as from 0.1 to 50 µm and for instance from 1 to 20 µm. The term "mean size" denotes the size given by the statistical particle size distribution to half of the population, noted as D50.

The filler with a specific surface area in accordance with one aspect of the disclosure herein may be chosen from organic and mineral fillers and mixtures thereof.

The organic filler may be chosen from polyolefinic waxes, for instance polyethylene waxes, such as those sold under the name "Performalen 2000®" by the company New Phase Technology, or from polymeric fillers such as polymethyl methacrylate (PMMA), for instance Jurymer MB1® sold by Nihon Junyaku or polytetrafluoroethylene (PTFE). Non-limiting illustrations of mineral fillers that may be mentioned include silicas, silicates, aluminas and aluminosilicates, such as those sold under the name "Sunsil 130®" by the company Sunjin Chemical or "Silica Beads SB 150®" by the company Miyoshi.

The particles of which the filler with a specific surface area is composed may have varied shapes. These particles may be globular, lamellar, spherical, hollow or solid. According to one aspect of the disclosure, the particles are hollow.

Thus, in the case of a mineral filler, hollow silica microspheres are suitable, such as "Sunsphere H-51" from Asahi Glass, with a specific surface area equal to 770 $m^2/g$, and "Sunsil 130" from Sunjin Chemical, with a specific surface area of 200-260 $m^2/g$.

According to one aspect of the disclosure, the composition comprises at least one tacky wax and at least one filler with a specific surface area of greater than or equal to 100 $m^2/g$, chosen from hollow spherical silica, hollow silica microspheres and polyethylene wax.

Dextrin Ester of Fatty Acid(s)

The dextrin esters of fatty acids that may be combined with the at least one tacky wax in the composition according to one aspect of the disclosure herein, is a dextrin monoester or polyester of at least one fatty acid, corresponding, for example, to the formula (II):

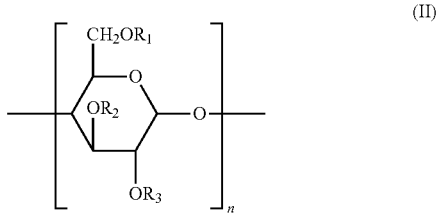

wherein:
n is an integer ranging from 3 to 200, for example, ranging from 20 to 150, and for further example ranging from 25 to 50,
the radicals $R_1$, $R_2$ and $R_3$, which may be identical or different, are chosen from hydrogen and acyl groups (R—CO—), wherein the acyl radical R is chosen from linear and branched, saturated and unsaturated hydrocarbon-based groups comprising from 7 to 29 carbon atoms, such as from 7 to 21, for example, from 11 to 19, for further example from 13 to 17, such as 15, carbon atoms, with the proviso that at least one of the said radicals $R_1$, $R_2$ or $R_3$ is other than hydrogen.

In one embodiment, $R_1$, $R_2$ and $R_3$ maybe chosen from hydrogen and acyl groups (R—CO—), wherein R is a hydrocarbon-based radical as defined above, with the proviso that at least two of the said radicals $R_1$, $R_2$ or $R_3$ are identical and other than hydrogen.

The radicals $R_1$, $R_2$ and $R_3$ may all comprise acyl groups (R—CO), which are identical or different. According to one aspect, the acyl groups are identical.

In another aspect, n ranges from 25 to 50, for example n is equal to 38, in the general formula (II) of the ester as disclosed herein.

When the radicals $R_1$, $R_2$ and $R_3$, which may be identical or different, comprise an acyl group (R—CO), these radicals may be chosen from at least one of caprylyl, caproyl, lauroyl, myristyl, palmityl, stearyl, eicosanyl, docosanoyl, isovaleryl, ethyl-2 butyryl, ethylmethylacetyl, isoheptanyl, ethyl-2 hexanyl, isononanyl, isodecanyl, isotridecanyl, isomyristyl, isopalmityl, isostearyl, isohexanyl, decenyl, dodecenyl, tetradecenyl, myristyl, hexadecenoyl, palmitoleyl, oleyl, elaidyl, eicosenyl, sorbyl, linoleyl, linolenyl, punicyl, arachidonyl, and stearolyl radicals.

In one aspect, at least one dextrin palmitate is used as the dextrin ester of fatty acid. This ester may be used alone or in a mixture with other esters.

In another embodiment, the dextrin ester of fatty acid has a degree of substitution of less than or equal to 2.5, for example, ranging from 1.5 to 2.5, such as from 2 to 2.5, on the basis of one glucose unit. The weight-average molecular weight of the dextrin ester may be from 10 000 to 150 000, such as from 12 000 to 100 000, or for instance, from 15 000 to 80 000.

Dextrin esters, such as dextrin palmitates, are commercially available under the name Rheopearl TL or Rheopearl KL by the company Chiba Flour.

The dextrin ester may be present in the composition as disclosed herein in an amount ranging from 0.1% to 20%, for instance from 0.5% to 15% by weight, and for example, from 1% to 10% by weight, relative to the total weight of the composition.

In another embodiment of the composition, the at least one tacky wax and the dextrin ester are present in an amount such that the weight ratio of the tacky wax relative to the dextrin ester ranges from 350 to 0.1, for example, from 100 to 0.5 and for further example from 50 to 1, such as from 15 to 2.

Physiologically Acceptable Medium

The physiologically acceptable medium of the composition may comprise a volatile solvent chosen from water and the volatile organic solvents and volatile oils defined below, and mixtures thereof.

The composition as disclosed herein may comprise an aqueous medium, constituting an aqueous phase, which may form the continuous phase of the composition.

The aqueous phase may essentially comprise water. It may also comprise a mixture of water and at least one water-miscible solvent (water miscibility of greater than 50% by weight at 25° C.), for instance lower monoalcohols comprising from 1 to 5 carbon atoms, such as ethanol or isopropanol, glycols comprising from 2 to 8 carbon atoms, such as propylene glycol, ethylene glycol, 1,3-butylene glycol or dipropylene glycol, $C_3$-$C_4$ ketones and $C_2$-$C_4$ aldehydes.

The aqueous phase (water and optionally the water-miscible organic solvent) may be present in an amount ranging from 1% to 95% by weight, for example ranging from 3% to 80% by weight, and for further example, ranging from 5% to 60% by weight, relative to the total weight of the composition.

The composition disclosed herein may comprise at least one oil and/or at least one organic solvent that may form a fatty phase, for example, a continuous fatty phase. The composition may be an anhydrous composition.

For the purposes of the disclosure herein, the expression "volatile oil or organic solvent" means any non-aqueous medium which can evaporate on contact with the skin or keratin material in less than one hour at room temperature and atmospheric pressure. The volatile organic solvent(s) and the volatile oils as disclosed herein, are volatile cosmetic organic solvents and oils that are liquid at room temperature, having a non-zero vapour pressure at room temperature and atmospheric pressure ranging from 0.13 Pa to 40 000 Pa ($10^{-3}$ to 300 mm Hg), for instance ranging from 1.3 Pa to 13 000 Pa (0.01 to 100 mm Hg), and for further instance ranging from 1.3 Pa to 1 300 Pa (0.01 to 10 mm Hg). The expression "non-volatile oil" means an oil which remains on the skin or keratin material at room temperature and atmospheric pressure for at least several hours and which has a vapour pressure of less than $10^{-3}$ mmHg (0.13 Pa).

These oils may be hydrocarbon-based oils, silicone oils, or mixtures thereof.

The expression "hydrocarbon-based oil" means an oil mainly comprising hydrogen and carbon atoms, and optionally at least one of oxygen, nitrogen, sulphur and/or phosphorus atoms. The volatile hydrocarbon-based oils may be chosen from hydrocarbon-based oils comprising from 8 to 16 carbon atoms, such as $C_8$-$C_{16}$ branched alkanes, for instance $C_8$-$C_{16}$ isoalkanes of petroleum origin (also known as isoparaffins), for instance isododecane (also known as 2,2,4,4,6-pentamethylheptane), isodecane and isohexadecane, and, for example, the oils sold under the trade names Isopars or Permetyls, $C_8$-$C_{16}$ branched esters, isohexyl neopentanoate, and mixtures thereof. Other volatile hydrocarbon-based oils, for instance petroleum distillates, such as those sold under the name Shell Solt by the company Shell, may also be used. The volatile solvent can be chosen from hydrocarbon-based volatile oils comprising from 8 to 16 carbon atoms, and mixtures thereof.

Volatile oils which may also be used are volatile silicones for example, linear or cyclic volatile silicone oils, such as those with a viscosity $\leq 6$ centistokes ($6 \times 10^{-6}$ m$^2$/s) and comprising from 2 to 10 silicon atoms, wherein these silicones may optionally comprise alkyl or alkoxy groups comprising from 1 to 22 carbon atoms. As volatile silicone oils which may be used in the invention, mention may be made of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, and mixtures thereof.

The volatile oil may be present in the composition as disclosed herein, in an amount ranging from 0% to 98% by weight, relative to the total weight of the composition, for example from 1% to 65% by weight.

The composition may also comprise at least one non-volatile oil chosen from non-volatile hydrocarbon-based oils and silicone oils.

Non-volatile hydrocarbon-based oils which may be mentioned include:

hydrocarbon-based plant oils such as triglycerides comprising fatty acid esters of glycerol, wherein the fatty acids may have varied chain lengths from $C_4$ to $C_{24}$, these chains possibly being linear or branched, and saturated or unsaturated; these oilscan be, for example, wheat germ oil, sunflower oil, grape seed oil, sesame oil, corn oil, apricot oil, castor oil, karite butter, avocado oil, olive oil, soybean oil, sweet almond oil, palm oil, rapeseed oil, cotton oil, hazelnut oil, macadamia oil, jojoba oil, alfalfa oil, poppy oil, pumpkin oil, marrow oil, blackcurrant seed oil, evening primrose oil, millet oil, barley oil, quinoa oil, rye oil, safflower oil, candlenut oil, passion flower oil and musk rose oil; or alternatively caprylic/capric acid triglycerides such as those sold by Stearineries Dubois or those sold under the names Miglyol 810, 812 and 818 by Dynamit Nobel;

synthetic ethers coomprising from 10 to 40 carbon atoms;

linear or branched hydrocarbons of mineral or synthetic origin, such as petroleum jelly, polydecenes, hydrogenated polyisobutene such as parleam, squalane, and mixtures thereof;

synthetic esters such as oils of formula $R_1COOR_2$ in which $R_1$ represents a linear or branched fatty acid residue coomprising from 1 to 40 carbon atoms and $R_2$ is chosen from branched hydrocarbon-based chains comprising from 1 to 40 carbon atoms, provided that $R_5+R_6 \geq 10$, such as, for example, purcellin oil (cetostearyl octanoate), isopropyl myristate, isopropyl palmitate, $C_{12}$-$C_{15}$ alkyl benzoate, hexyl laurate, diisopropyl adipate, isononyl isononanoate, 2-ethylhexyl palmitate, isostearyl isostearate, alkyl or polyalkyl octanoates, decanoates or ricinoleates such as propylene glycol dioctanoate; hydroxylated esters such as isostearyl lactate and diisostearyl malate; and pentaerythritol esters;

fatty alcohols that are liquid at room temperature, comprising a branched and/or unsaturated carbon-based chain comprising from 12 to 26 carbon atoms, for instance octyldodecanol, isostearyl alcohol, oleyl alcohol, 2-hexyldecanol, 2-butyloctanol or 2-undecylpentadecanol;

higher fatty acids such as oleic acid, linoleic acid or linolenic acid; and mixtures thereof.

The non-volatile silicone oils which may be used in the composition according to one embodiment of the disclosure may be non-volatile polydimethylsiloxanes (PDMSs), polydimethylsiloxanes comprising alkyl or alkoxy groups that are pendent and/or at the end of a silicone chain, wherein the groups each comprise from 2 to 24 carbon atoms, phenylsilicones, for instance phenyltrimethicones, phenyldimethicones, phenyl-trimethylsiloxydiphenylsiloxanes, diphenyldimethicones, diphenylmethyldiphenyltrisiloxanes and 2-phenylethyl trimethylsiloxysilicates.

The non-volatile oils may be present in the composition as disclosed herein in an amount ranging from 0 to 50% (such as from 0.1% to 50%) by weight, for example, from 0 to 40% by weight (such as 0.1% to 40%) and for further example from 0 to 30% by weight (such as 0.1% to 30%), relative to the total weight of the composition.

According to one aspect as disclosed herein, the composition may also comprise an additional wax other than the at least one tacky wax and the at least one additional wax, or hard wax, described above. The further additional wax may be chosen, for example, from beeswax, paraffin waxes, hydrogenated castor oil and silicone waxes.

The further additional wax may be present in the form of a wax microdispersion as described above for the first (e.g., tacky) and the second (e.g., hard) wax.

The further additional wax may be present in the composition disclosed herein in an amount ranging from 0.1% to 50% by weight, relative to the total weight of the composition, for example, from 0.5% to 30% by weight, such as from 1% to 20% by weight.

The total content of waxes (first wax and/or second wax and/or additional wax) in the composition as disclosed herein may range from 5% to 70% by weight, for instance from 10% to 60% and for further instance from 15% to 50% by weight, relative to the total weight of the composition.

In yet another aspect as disclosed herein, the composition may comprise at least one fatty compound that is pasty at room temperature. For the purposes of the present disclosure, the expression "pasty fatty substance" means fatty substances with a melting point ranging from 20 to 55° C., such as 25 to 45° C., and/or a viscosity at 40° C. ranging from 0.1 to 40 Pa·s (1 to 400 poises), such as 0.5 to 25 Pa·s, measured using a Contraves TV or Rheomat 80 viscometer, equipped with a spindle rotating at 60 Hz. A person of ordinary skill in the art can select the spindle for measuring the viscosity from the spindles MS-r3 and MS-r4, on the basis of his general knowledge, so as to be able to carry out the measurement of the pasty compound tested.

These fatty substances can be hydrocarbon-based compounds, optionally of polymeric type; they can also be chosen from silicone compounds; they may also be in the form of a mixture of hydrocarbon-based compounds and/or silicone compounds. In the case of a mixture of different pasty fatty substances, mention may be made of the hydrocarbon-based pasty compounds (comprising mainly hydrogen and carbon atoms and optionally ester groups) used in major proportion.

Among the pasty compounds which may be used in the composition as disclosed herein, mention may be made of lanolins and lanolin derivatives such as acetylated lanolins or oxypropylenated lanolins or isopropyl lanolate, having a viscosity ranging from 18 to 21 Pa·s, such as 19 to 20.5 Pa·s, and/or a melting point ranging from 30 to 55° C., and mixtures thereof. It is also possible to use esters of fatty acids or of fatty alcohols, for example those comprising from 20 to 65 carbon atoms (melting point ranging from about 20 to 35° C. and/or viscosity at 40° C. ranging from 0.1 to 40 Pa·s), such as triisostearyl or cetyl citrate; arachidyl propionate; polyvinyl laurate; cholesterol esters, such as triglycerides of plant origin, such as hydrogenated plant oils, viscous polyesters such as poly(12-hydroxystearic acid), and mixtures thereof.

Mention may also be made of pasty silicone fatty substances such as polydimethylsiloxanes (PDMSs) comprising pendent chains of the alkyl or alkoxy type comprising from 8 to 24 carbon atoms, and having a melting point ranging from 20-55° C., such as stearyldimethicones, for instance those sold by Dow Corning under the trade names DC2503 and DC25514, and mixtures thereof.

The pasty fatty substance may be present in the composition as disclosed in a proportion ranging from 0.01% to 60% by weight, relative to the total weight of the composition, for example in a proportion ranging from 0.5% to 45% by weight, and for further example, ranging from 2% to 30% by weight, relative to the total weight of the composition.

As disclosed herein, the composition can contain emulsifying surfactants, present in a proportion ranging from 2% to 30% by weight relative to the total weight of the composition, and such as from 5% to 15%. These surfactants may be chosen from anionic and nonionic surfactants. Reference may be made to the document "Encyclopedia of Chemical Technology, Kirk-Othmer", volume 22, pp. 333-432, 3rd edition, 1979, Wiley, for the definition of the properties and functions (emulsifying) of surfactants, in particular pp. 347-377 of the said reference, for the anionic and nonionic surfactants.

Suitable non-limiting examples of surfactants that may be used in the composition include:

nonionic surfactants: fatty acids, fatty alcohols, polyethoxylated and polyglycerolated fatty alcohols such as polyethoxylated stearyl and cetylstearyl alcohol, fatty acid esters of sucrose, alkylglucose esters, such as polyoxyethylenated fatty esters of $C_1$-$C_6$ alkyl glucose, and mixtures thereof;

anionic surfactants: $C_{16}$-$C_{30}$ fatty acids neutralized with amines, aqueous ammonia, or alkaline salts, and mixtures thereof.

Mention may also be made of surfactants which make it possible to obtain an oil-in-water or wax-in-water emulsion.

In still another embodiment of the composition disclosed herein, the composition can comprise at least one film-forming polymer.

The film-forming polymer may be present in the composition in a solids content ranging from 0.1% to 60% by weight relative to the total weight of the composition, for example, from 0.5% to 40% by weight and for further example, from 1% to 30% by weight.

In the present disclosure, the expression "film-forming polymer" means a polymer which is capable, by itself or in the presence of an auxiliary film-forming agent, of forming a continuous and adherent film on a support, for example on keratin materials.

Among the film-forming polymers which may be used, mention may be made of synthetic polymers, of radical-mediated type or of polycondensate type, polymers of natural origin, and mixtures thereof.

The expression "radical-mediated film-forming polymer" means a polymer obtained by polymerization of monomers comprising unsaturation, such as ethylenic unsaturation, each monomer being capable of homopolymerizing (unlike polycondensates).

The film-forming polymers of radical-mediated type may be, in particular, vinyl polymers or copolymers, for instance acrylic polymers.

The vinyl film-forming polymers can result from the polymerization of monomers comprising ethylenic unsaturation and comprising at least one acidic group and/or esters of these acidic monomers and/or amides of these acidic monomers.

Monomers bearing an acidic group which may be used are α,β-ethylenic unsaturated carboxylic acids such as those chosen from acrylic acid, methacrylic acid, crotonic acid, maleic acid and itaconic acid. Mention may be made of (meth)acrylic acid and crotonic acid. According to one aspect of the disclosure, (meth)acrylic acid may be used.

Mention may also be made of the esters of acidic monomers chosen from (meth)acrylic acid esters (also known as (meth)acrylates), such as (meth)acrylates of an alkyl, for example, of a $C_1$-$C_{30}$ and $C_1$-$C_{20}$ alkyl, (meth)acrylates of an aryl, for example, of a $C_6$-$C_{10}$ aryl, and (meth)acrylates of a hydroxyalkyl, such as of a $C_2$-$C_6$ hydroxyalkyl.

Among the alkyl (meth)acrylates which may be mentioned are methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl (meth)acrylates which may be mentioned are hydroxyethyl acrylate, 2-hydroxypropyl acrylate, hydroxyethyl methacrylate and 2-hydroxypropyl methacrylate.

Among the aryl (meth)acrylates which may be mentioned are benzyl acrylate and phenyl acrylate.

Among the (meth)acrylic acid esters, mention may be made of alkyl (meth)acrylates.

As disclosed herein, the alkyl group of the esters may be either fluorinated or perfluorinated, i.e. some or all of the hydrogen atoms of the alkyl group may be substituted with fluorine atoms.

Examples of amides of the acid monomers that may be mentioned are (meth)acrylamides, such as N-alkyl(meth) acrylamides, such as $C_2$-$C_{12}$ alkyls. Among the N-alkyl (meth)acrylamides that may be mentioned are N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. These monomers may be polymerized with acid monomers and/or esters thereof and/or amides thereof, such as those mentioned above.

Examples of vinyl esters that may be mentioned are vinyl acetate, vinyl neodecanoate, vinyl pivalate, vinyl benzoate and vinyl t-butylbenzoate.

Examples of styrene monomers that may be mentioned are styrene and α-methylstyrene.

Among the film-forming polycondensates that may be mentioned are polyurethanes, polyesters, polyesteramides, polyamides, epoxyester resins and polyureas.

The polyurethanes may be chosen from anionic, cationic, nonionic and amphoteric polyurethanes, polyurethane-acrylics, polyurethane-polyvinylpyrrolidones, polyester-polyurethanes, polyether-polyurethanes, polyureas and polyurea/polyurethanes, and mixtures thereof.

The polyesters may be obtained, in a known manner, by polycondensation of dicarboxylic acids with polyols, for example diols.

The dicarboxylic acid may be aliphatic, alicyclic or aromatic. Examples of such acids that may be mentioned are: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid or 2,6-naphthalenedicarboxylic acid. These dicarboxylic acid monomers may be used alone or as a combination of at least two dicarboxylic acid monomers. Among these monomers, mention may be made of phthalic acid, isophthalic acid and terephthalic acid.

The diol may be chosen from aliphatic, alicyclic and aromatic diols. Mention may be made of the following diols: ethylene glycol, diethylene glycol, triethylene glycol, 1,3-propanediol, cyclohexanedimethanol and 4-butanediol. Other polyols that may be used are glycerol, pentaerythritol, sorbitol, and trimethylolpropane.

The polyesteramides may be obtained in a manner analogous to that of the polyesters, by polycondensation of diacids with diamines or amino alcohols. Diamines which may be used include, for example, ethylenediamine, hexamethylenediamine and meta- or para-phenylenediamine. An amino alcohol which may be used is monoethanolamine.

The polyester may also comprise at least one monomer bearing at least one group —$SO_3M$, wherein M is chosen from hydrogen atoms, ammonium ions $NH_4^+$, and metal ions such as, for example, $Na^+$, $Li^+$, $K^+$, $Mg^{2+}$, $Ca^{2+}$, $Cu^{2+}$, $Fe^{2+}$ and $Fe^{3+}$. Mention may be made of a difunctional aromatic monomer comprising a group —$SO_3M$.

The aromatic nucleus of the difunctional aromatic monomer also bearing a group —$SO_3M$ as described above may be chosen, for example, from benzene, naphthalene, anthracene, biphenyl, oxybiphenyl, sulphonylbiphenyl and methylenebiphenyl nuclei. As examples of difunctional aromatic monomers also bearing a group —$SO_3M$, mention may be made of: sulphoisophthalic acid, sulphoterephthalic acid, sulphophthalic acid, and 4-sulphonaphthalene-2,7-dicarboxylic acid.

The copolymers that may be used include, for example, those based on isophthalate/sulphoisophthalate, such as copolymers obtained by condensation of diethylene glycol, cyclohexanedimethanol, isophthalic acid and sulphoisophthalic acid.

The polymers of natural origin, optionally modified, may be chosen from, for example, shellac resin, sandarac gum, dammar resins, elemi gums, copal resins and cellulose polymers, and mixtures thereof.

According to one aspect of the composition as disclosed herein, the film-forming polymer may be a water-soluble polymer and may be present in an aqueous phase of the composition; the polymer is thus solubilized in the aqueous phase of the composition. Examples of water-soluble film-forming polymers which may be mentioned are:

proteins, for instance proteins of plant origin such as wheat proteins and soybean proteins; proteins of animal origin such as keratins, for example keratin hydrolysates and sulphonic keratins;

polymers of celluloses such as hydroxyethylcellulose, hydroxypropylcellulose, methylcellulose, ethylhydroxyethylcellulose and carboxymethylcellulose, and quaternized cellulose derivatives;

acrylic polymers or copolymers, such as polyacrylates or polymethacrylates;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;

polymers of natural origin, which are optionally modified, such as:
gum arabics, guar gum, xanthan derivatives, karaya gum;
alginates and carrageenans;
glycoaminoglycans, hyaluronic acid and derivatives thereof;
shellac resin, sandarac gum, dammar resins, elemi gums and copal resins;
deoxyribonucleic acid;
mucopolysaccharides such as chondroitin sulphate,
and mixtures thereof.

According to another embodiment of the composition as disclosed herein, the film-forming polymer may be present in a liquid fatty phase comprising organic solvents or oils such as those described above (the film-forming polymer is thus said to be a liposoluble polymer). For the purposes this disclosure, the expression "liquid fatty phase" means a fatty phase which is liquid at room temperature (25° C.) and atmospheric pressure (760 mmHg, i.e. $10^5$ Pa), composed of one or more fatty substances that are liquid at room temperature, also known as oils, which are generally mutually compatible.

The liquid fatty phase may comprise a volatile oil, optionally mixed with a non-volatile oil, the oils possibly being chosen from those mentioned above.

Examples of liposoluble polymers which may be mentioned are copolymers of vinyl ester (the vinyl group being directly linked to the oxygen atom of the ester group and the vinyl ester comprising a saturated, linear or branched hydrocarbon-based radical of 1 to 19 carbon atoms, linked to the carbonyl of the ester group) and of at least one other monomer which may be a vinyl ester (other than the vinyl ester already present), an α-olefin (comprising from 8 to 28 carbon atoms), an alkyl vinyl ether (wherein the alkyl group comprises from 2 to 18 carbon atoms) or an allylic or methallylic ester (comprising a saturated, linear or branched hydrocarbon-based radical of 1 to 19 carbon atoms, linked to the carbonyl of the ester group).

These copolymers may be crosslinked with the aid of crosslinking agents that may be either of the vinyl type or of the allylic or methallylic type, such as tetraallyloxyethane, divinylbenzene, divinyl octanedioate, divinyl dodecanedioate and divinyl octadecanedioate.

Examples of these copolymers that may be mentioned are the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetaallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Examples of liposoluble film-forming polymers which may also be mentioned are liposoluble copolymers, for example, those resulting from the copolymerization of vinyl esters comprising from 9 to 22 carbon atoms or of alkyl acrylates or methacrylates, and alkyl radicals comprising from 10 to 20 carbon atoms.

Such liposoluble copolymers may be chosen from those obtained from polyvinyl stearate, polyvinyl stearate crosslinked with divinylbenzene, with diallyl ether or with diallyl phthalate, polystearyl (meth)acrylate, polyvinyl laurate and polylauryl (meth)acrylate, it being possible for these poly(meth)acrylates to be crosslinked with the aid of ethylene glycol dimethacrylate or tetraethylene glycol dimethacrylate.

The liposoluble copolymers defined above are known and are described in patent application FR-A-2 232 303; they may have a weight-average molecular weight ranging from 2 000 to 500 000, for instance, from 4 000 to 200 000.

As liposoluble film-forming polymers that may be used in the invention, mention may also be made of polyalkylenes for example, copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP), for instance, copolymers of vinylpyrrolidone and of $C_2$ to $C_{40}$ and better still $C_3$ to $C_{20}$ alkene. As examples of VP copolymers that may be used in accordance with the present disclosure, mention may be made of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

The film-forming polymer may also be present in the composition in the form of particles dispersed in an aqueous phase or in a non-aqueous solvent phase, which is generally known as a latex or pseudolatex. The techniques for preparing these dispersions are well known to those of ordinary skill in the art.

Aqueous dispersions of film-forming polymers which may be used are the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® by the company Daito Kasey Kogyo; or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulphopolyesters sold under the brand name "Eastman AQ®" by the company Eastman Chemical Products, vinyl dispersions, for instance "Mexomer PAM" and also acrylic dispersions in isododecane, for instance "Mexomer PAP" by the company Chimex.

The composition as disclosed herein may comprise a plasticizer, which promotes the formation of a film with the film-forming polymer. Such a plasticizer may be chosen from any of the compounds known to those of ordinary skill in the art as being capable of satisfying the desired function.

Additives

The composition as disclosed herein may also comprise a dyestuff, for instance pulverulent dyestuffs, liposoluble dyes and water-soluble dyes. This dyestuff may be present in an amount ranging from 0.01% to 30% by weight, relative to the total weight of the composition.

The pulverulent dyestuffs may be chosen from pigments and nacres.

The pigments may be white or coloured, mineral and/or organic, and coated or uncoated. Among the mineral pigments which may be mentioned are titanium dioxide, optionally surface-treated, zirconium oxide, zinc oxide or cerium oxide, as well as iron oxide, chromium oxide, manganese violet, ultramarine blue, chromium hydrate and ferric blue. Among the organic pigments which may be mentioned are carbon black, pigments of D & C type, and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with, for example, ferric blue or chromium oxide, titanium mica with an organic pigment of the above mentioned type, and nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto. The water-soluble dyes are, for example, beetroot juice, methylene blue, the disodium salt of ponceau, the disodium salt of alizarin green, quinoline yellow, the trisodium salt of amaranthus, the disodium salt of tartrazine, the monosodium salt of rhodamine, the disodium salt of fuchsin, and xanthophyll.

The composition as disclosed herein may also comprise any additive usually used in cosmetics, such as antioxidants, fillers, preserving agents, fragrances, neutralizers, thickeners, vitamins and plasticizers, and mixtures thereof.

According to one particular aspect of the composition disclosed herein, the composition contains no UV-screening agent (organic screening agent or mineral screening agent; screening agent that absorbs or reflects ultraviolet radiation).

Needless to say, a person skilled in the art will take care to select the optional additional additives and/or the amount thereof such that the advantageous properties of the composition according to this disclosure are not, or are not substantially, adversely affected by the addition envisaged.

The composition as disclosed herein may be manufactured by the known processes generally used in cosmetics.

One aspect of the composition disclosed herein, is a composition for coating keratin fibres, for example a mascara, which may be packaged in an applicator product comprising a reservoir and a removable means for closing the said reservoir, for instance, in a leaktight manner.

The said applicator assembly may also comprise a member for applying the makeup composition to the keratin fibres, for example the eyelashes, the said applicator member allowing the composition to be taken up and allowing the composition taken up to be deposited on the eyelashes. This applicator member may be securely fastened to the means for leaktight closure of the assembly.

The applicator assembly may also comprise a draining member (or drainer) for the said applicator member, the draining member possibly being securely fastened to the reservoir.

The applicator member may be a mascara brush that is known to those skilled in the art. Such a brush comprises bristles arranged radially around a twisted core, for example a metal core. The brush may be of varied shape and may comprise cutout sections. Mascara brushes are described, for example, in documents FR-A-2 607 373, EP-A-611 170, EP-A-811 336, EP-A-811 337 and EP-A-842 620.

FIG. 1, to which reference is now made, shows one embodiment of a packaging and applicator assembly 1 containing a mascara composition according to the disclosure.

The packaging and applicator assembly 1 comprises a container 2 on which is mounted a threaded neck 3, one free edge of which delimits an aperture 4. In the aperture 4 is mounted a draining member 5. The assembly 1 also comprises an applicator device 10 comprising a cap 11 securely fastened to a stem 13, one end of which comprises an applicator 12, generally configured in the form of an arrangement of fibres held between the two branches of a twisted iron wire. An inner surface of the cap 11 is threaded so as to engage with the threading of the neck 3. Thus, when the applicator 12 and the stem 13 are placed inside the container 2, the threading of the cap 11 engages with the threading of the neck 3 such that the cap closes the aperture 4 of the container in a leaktight manner.

Alternatively, the applicator may be a comb generally comprising a plurality of teeth obtained by moulding with a support made of thermoplastic material. The applicator may combine a comb with a brush.

The present disclosure is illustrated in greater detail in the examples that follow.

EXAMPLES 1 TO 6

An anhydrous mascara according to the disclosure above (Example 1) and 5 mascaras not forming part of the invention (Examples 2 to 6) having the composition below were prepared, using 6 different waxes:

| | |
|---|---|
| wax | 27 g |
| bentonite | 5.3 g |
| propylene carbonate | 1.7 g |
| vinyl acetate/allyl stearate copolymer (65/35) (Mexomer PQ from Chimex) | 2.2 g |
| polyvinyl laurate (Mexomer PP from Chimex) | 0.7 g |
| silica | 0.8 g |
| pigments | 3.6 g |
| preserving agents | qs |
| isododecane | qs 100 g |

For each composition, the viscosity and the consistency index were measured, and the stability at 25° C. was evaluated.

The viscosity measurement was performed at 25° C. using a Rheomat RM 180 viscometer equipped with a No. 4 spindle, the measurement being performed after rotation of the spindle for 10 minutes (after which time stabilization of the viscosity and of the rotation speed of the spindle were observed), at a shear rate of $200 \text{ s}^{-1}$.

The consistency index measurement was performed using a TA-XT2i texturometer from the company Rheo, equipped with a stainless-steel cylindrical probe 12 mm in diameter.

A cylindrical container (35 mm in diameter and 15 mm deep) was filled with the mascara composition to be tested and the surface of the product contained in the container was then levelled off to obtain a totally flat surface of the product. The cylindrical probe of the texturometer was displaced at a speed of $10 \text{ mm·s}^{-1}$ and then penetrated the mascara contained in the cylindrical container, to a depth of 0.2 mm. The force exerted by the mascara on the probe was then measured, this force corresponding to the consistency index of the mascara, expressed in Pa.

The stability was evaluated by visual observation of the composition after storage for two weeks at 25° C.

The tack and the hardness of the wax were measured according to the measuring method described previously above.

The following results were obtained:

| Example | Wax | Tack (N · s) | Hardness (MPa) | Viscosity (Pa · s) | Consistency (Pa) | Stability |
|---|---|---|---|---|---|---|
| 1 | Koster K 82 P | 3.38 | 0.96 | 3.6 | 560 | Yes |
| 2 | Beeswax | 2.02 | 3.68 | 5.9 | 1 842 | Yes |
| 3 | Hydrogenated jojoba oil | 0.18 | 8.62 | 12.8 | 1 991 | Yes |
| 4 | Hydrogenated castor oil | 0.08 | 2.77 | Too thick | 22 942 | — |
| 5 | Orange oil[1] | 0.09 | 0.09 | <1 | Too fluid | No 2 phases |
| 6 | Oxypropylenated (5 PO) lanolin wax[2] | 0.14 | 0.06 | <1 | Too fluid | No 2 phases |

[1] sold by the company Koster Keunen
[2] Emery 1695 from the company Cognis

It was found that composition 1 as disclosed herein was stable and had the lowest viscosity and the lowest consistency. Compositions 2 and 3, although stable, had a higher viscosity and a higher consistency than those of composition 1. Composition 4 was too thick and is therefore unsuitable for application to the eyelashes using a mascara brush.

Compositions 5 and 6 were not stable: they showed 2 phases after two weeks of storage at 25° C.

EXAMPLE 7

A wax-in-water emulsion mascara having the composition below was prepared:

| | |
|---|---|
| tacky wax (Kester Wax K 82 P from the company Koster Keunen) | 28 g |
| 2-amino-2-methyl-1,3-propanediol | 0.5 g |
| triethanolamine | 2.4 g |
| stearic acid | 5.8 g |
| water-soluble nonionic polymers | 4.3 g |
| sodium polymethacrylate (Darvan 7 from the company Vanderbilt) | 0.25 g AM |
| hydroxyethylcellulose crosslinked with epichlorohydrin, quaternized with trimethylamine (JR 400 from the company Union Carbide) | 0.1 g |
| pigments | 5.4 g |
| preserving agents | qs |
| water | qs 100 g |

This mascara was stable after 24 hours at room temperature. It applied easily and adhered well to the eyelashes. The mascara formed a smooth, uniform makeup and thickened the eyelashes.

EXAMPLE 8

An anhydrous mascara having the composition below was prepared:

| | |
|---|---|
| tacky wax (Kester Wax K 82 P from the company Koster Keunen) | 30 g |
| bentonite | 5.3 g |
| propylene carbonate | 1.7 g |
| vinyl acetate/allyl stearate copolymer (65/35) (Mexomer PQ from Chimex) | 2.2 g |
| polyvinyl laurate (Mexomer PP from Chimex) | 0.7 g |
| stearate of the oligomer of 12-hydroxy-stearic acid (Solsperse 21000 from Avecia) | 0.1 g |
| filler | 0.8 g |
| pigments | 4.2 g |
| preserving agents | qs |
| isododecane | qs 100 g |

This waterproof mascara adhered well to the eyelashes. It gave the eyelashes a highly separating, smooth, uniform makeup.

EXAMPLE 9

An anhydrous mascara having the composition below was prepared:

| | |
|---|---|
| tacky wax (Kester Wax K 82 P from the company Koster Keunen) | 35 g |
| bentonite | 5.3 g |
| propylene carbonate | 1.7 g |
| vinyl acetate/allyl stearate copolymer (65/35) (Mexomer PQ from Chimex) | 2.2 g |
| polyvinyl laurate (Mexomer PP from Chimex) | 0.7 g |
| stearate of the oligomer of 12-hydroxy-stearic acid (Solsperse 21000 from Avecia) | 0.1 g |
| filler | 0.8 g |
| pigments | 4.2 g |
| preserving agents | qs |
| isododecane | qs 100 g |

This waterproof mascara adhered well to the eyelashes. It gave the eyelashes a highly separated, smooth, uniform makeup.

EXAMPLE 10

A wax-in-water emulsion mascara having the composition below was prepared:

| | |
|---|---|
| tacky wax (Kester Wax K 82 P from the company Koster Keunen) | 27 g |
| carnauba wax | 3 g |
| 2-amino-2-methyl-1,3-propanediol | 0.5 g |
| triethanolamine | 2.4 g |
| stearic acid | 5.8 g |
| water-soluble nonionic polymers | 4.3 g |
| sodium polymethacrylate (Darvan 7 from the company Vanderbilt) | 0.25 g AM |
| hydroxyethylcellulose crosslinked with epichlorohydrin, quaternized with trimethylamine (JR 400 from the company Union Carbide) | 0.1 g |
| pigments | 5.4 g |
| preserving agents | qs |
| water | qs 100 g |

This mascara was stable after 24 hours at room temperature. It applied easily and adhered well to the eyelashes. The mascara formed a smooth, uniform makeup and thickened the eyelashes.

EXAMPLES 11 TO 13

The anhydrous mascaras below were prepared:

| | |
|---|---|
| tacky wax (Kester Wax K 82 P ® from the company Koster Keunen) | 27 g |
| bentonite | 2.66 g |
| propylene carbonate | 1.7 g |
| vinyl acetate/allyl stearate copolymer (65/35) (Mexomer PQ ® from Chimex) | 2.2 g |
| polyvinyl laurate (Mexomer PP ® from Chimex) | 0.7 g |
| stearate of the oligomer of 12-hydroxy-stearic acid (Solsperse 21000 ® from Avecia) | 0.1 g |
| filler with a specific surface area | 15 g |
| pigments | 4.2 g |
| preserving agents | qs |
| isododecane | qs 100 g |

Using this formulation, three different mascaras in accordance with the disclosure herein were prepared, incorporating a specific filler into each of them.

The nature of the three fillers chosen, their specificities and the respective amounts are given in Table 1.

The silica Sunsil 130® is sold by Sunjin Chemical.

The polymethyl methacrylate Jurymer MB1® is sold by Nihon Junyakuet, and the silica Sunsphere H-51® is sold by Asahi Glass.

The tack is evaluated according to the following protocol:

A sample consisting of straight hairs (60 hairs 15 mm long) was made up by applying the product in 30 successive sweeps with a brush. After drying for one hour, the made-up hairs were rubbed with a finger, by means of a to and fro motion. The tack was assessed qualitatively according to the degree of stuck hairs, from 1 (not stuck at all) to 5 (very stuck).

The three waterproof mascaras thus obtained adhered well to the eyelashes. They gave the eyelashes a highly separated, smooth, uniform makeup.

EXAMPLE 14

An anhydrous waterproof mascara having the composition below was prepared:

| | |
|---|---|
| Tacky wax (Kester Wax K 82 P ® from the company Koster Keunen) | 32 g |
| Dextrin palmitate (Rheopearl KL ® from Chiba Flour) | 5.3 g |
| Vinyl acetate/allyl stearate copolymer (65/35) (Mexomer PQ ® from Chimex) | 2.2 g |
| Polyvinyl laurate (Mexomer PP ® from Chimex) | 0.75 g |
| Stearate of the oligomer of 12-hydroxystearic acid (Solsperse 21000 ® from Avecia) | 0.1 g |
| Silica | 10 g |
| Talc | 0.84 g |
| Pigments | 4.6 g |
| Preserving agents | qs |
| Isododecane | qs 100 g |

The mascara applied easily to the eyelashes and gave the eyelashes a thick, non-tacky makeup: the eyelashes were well separated.

EXAMPLE 15

A wax/water emulsion mascara having the composition below was prepared:

| | |
|---|---|
| Tacky wax (Kester Wax K 82 P ® from the company Koster Keunen) | 27 g |
| Candelilla wax | 5 g |
| Dextrin palmitate (Rheopearl KL ® from Chiba Flour) | 6 g |
| Stearic acid | 5.8 g |
| 2-Amino-2-methyl-1,3-propanediol | 0.5 g |
| Triethanolamine | 2.4 g |
| Hydroxyethylcellulose | 0.9 g |
| Silica | 5 g |
| Pigments | 5.5 g |
| Preserving agents | qs |
| Water | qs 100 g |

The mascara applied very easily to the eyelashes and gave a charging and separating uniform deposit.

What is claimed is:

1. A process for obtaining a charging and separating makeup result on the eyelashes comprising applying to the eyelashes a composition comprising, in a cosmetically acceptable medium, at least one wax in an amount of at least 27% by weight, relative to the total weight of the composition, wherein said at least one wax has a tack of greater than or equal to 0.7 N·s and a hardness of less than or equal to 3.5 MPa, and wherein the at least one wax is a compound of formula (I):

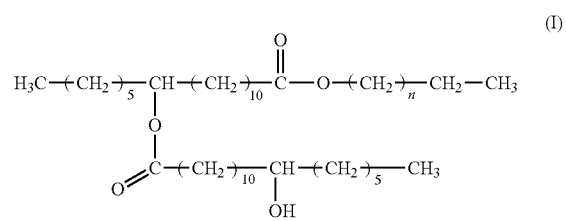

wherein n is an integer ranging from 18 to 38.

2. The process according to claim 1, wherein the at least one wax has a tack ranging from 0.7 N·s to 30 N·s.

3. The process according to claim 2, wherein the at least one wax has a tack ranging from 1 N·s to 30 N·s.

4. The process according to claim 3, wherein the at least one wax has a tack ranging from 1 N·s to 20 N·s.

5. The process according to claim 4, wherein the at least one wax has a tack ranging from 2 N·s to 20 N·s.

6. The process according to claim 5, wherein the at least one wax has a tack ranging from 2 N·s to 10 N·s.

7. The process according to claim 1, wherein the at least one wax has a hardness ranging from 0.01 to 3.5 MPa.

8. The process according to claim 7, wherein the at least one wax has a hardness ranging from 0.05 MPa to 3 MPa.

9. The process according to claim 8, wherein the at least one wax has a hardness ranging from 0.1 MPa to 2.5 MPa.

10. The process according to claim 1, wherein the at least one wax is present in an amount ranging from 27% to 60% by weight, relative to the total weight of the composition.

11. The process according to claim 10, wherein the at least one wax is present in an amount ranging from 28% to 50% by weight, relative to the total weight of the composition.

12. The process according to claim 11, wherein the at least one wax is present in an amount ranging from 30% to 40% by weight, relative to the total weight of the composition.

13. The process according to claim 1, wherein the composition further comprises at least one additional wax with a hardness of greater than or equal to 6 MPa.

TABLE I

| Example (Formula) | Trade name | Chemical nature | Mass (g) | Size of the filler μm | Specific surface area m²/g | Tack after rubbing on samples |
|---|---|---|---|---|---|---|
| No. 1 | Sunsil 130 ® | Hollow, spherical silica | 15 | 6-9 | 200-260 | 1 |
| No. 2 | Jurymer MB1 ® | Polymethyl methacrylate | 15 | 8-15 | 300 | 2 |
| No. 3 | Sunsphere ® H-51 | Hollow silica microspheres | 15 | 5 | 770 | 1 |

14. The process according to claim 13, wherein the at least one additional wax has a hardness ranging from 6 MPa to 30 MPa.

15. The process according to claim 14, wherein the at least one additional wax has a hardness ranging from 7 MPa to 25 MPa.

16. The process according to claim 15, wherein the at least one additional wax has a hardness ranging from 8 MPa to 25 MPa.

17. The process according to claim 16, wherein the at least one additional wax has a hardness ranging from 9 to 20 MPa.

18. The process according to claim 17, wherein the at least one additional wax has a hardness ranging from 10 MPa to 20 MPa.

19. The process according to claim 13, wherein the at least one additional wax is chosen from carnauba wax, polyethylene waxes, candelilla wax, hydrogenated jojoba oil, bis(1,1,1-trimethylolpropane) tetrastearate, and a wax obtained by hydrogenation of olive oil esterified with stearyl alcohol.

20. The process according to claim 13, wherein the at least one additional wax is present in an amount ranging from 0.1% to 30% by weight, relative to the total weight of the composition.

21. The process according to claim 20, wherein the at least one additional wax is present in an amount ranging from 1% to 20% by weight, relative to the total weight of the composition.

22. The process according to claim 21, wherein the at least one additional wax is present in an amount ranging from 2% to 10% by weight, relative to the total weight of the composition.

23. The process according to claim 1, wherein the composition further comprises an aqueous phase.

24. The process according to claim 23, wherein the aqueous phase is chosen from those formed from water and from those that are a mixture of water and water-miscible organic solvents.

25. The process according to claim 24, wherein the water-miscible organic solvent is chosen from lower monoalcohols comprising from 1 to 5 carbon atoms, glycols comprising from 2 to 8 carbon atoms, $C_3$-$C_4$ ketones, and $C_2$-$C_4$ aldehydes.

26. The process according to claim 25, wherein the aqueous phase is present in an amount ranging from 1% to 95% by weight, relative to the total weight of the composition.

27. The process according to claim 26, wherein the aqueous phase is present in an amount ranging from 3% to 80% by weight, relative to the total weight of the composition.

28. The process according to claim 27, wherein the aqueous phase is present in an amount ranging from 5% to 60% by weight, relative to the total weight of the composition.

29. The process according to claim 1, wherein the composition further comprises at least one volatile oil.

30. The process according to claim 29, wherein the at least one volatile oil is chosen from hydrocarbon-based oils and silicone oils.

31. The process according to claim 30, wherein the at least one volatile oil is present in an amount ranging from 0.1% to 98% by weight, relative to the total weight of the composition.

32. The process according to claim 31, wherein the at least one volatile oil is present in an amount ranging from 1% to 65% by weight, relative to the total weight of the composition.

33. The process according to claim 1, wherein the composition further comprises at least one non-volatile oil.

34. The process according to claim 33, wherein the at least one non-volatile oil is present in an amount ranging from 0.1% to 50% by weight, relative to the total weight of the composition.

35. The process according to claim 34, wherein the at least one non-volatile oil is present in an amount ranging from 0.1% to 40% by weight, relative to the total weight of the composition.

36. The process according to claim 35, wherein the at least one non-volatile oil is present in an amount ranging from 0.1% to 30% by weight, relative to the total weight of the composition.

37. The process according to claim 1, wherein the composition further comprises at least one film-forming polymer.

38. The process according to claim 37, wherein the at least one film-forming polymer is present in a solids content ranging from 0.1% to 60% by weight, relative to the total weight of the composition.

39. The process according to claim 38, wherein the at least one film-forming polymer is present in a solids content ranging from 0.5% to 40% by weight, relative to the total weight of the composition.

40. The process according to claim 39, wherein the at least one film-forming polymer is present in a solids content ranging from 1% to 30% by weight, relative to the total weight of the composition.

41. The process according to claim 1, wherein the composition further comprises at least one additional wax.

42. The process according to claim 41, wherein the at least one additional wax is present in an amount ranging from 0.1% to 50% by weight, relative to the total weight of the composition.

43. The process according to claim 42, wherein the at least one additional wax is present in an amount ranging from 0.5% to 30% by weight, relative to the total weight of the composition.

44. The process according to claim 43, wherein the additional wax is present in an amount ranging from 1% to 20% by weight, relative to the total weight of the composition.

45. The process according to claim 44, wherein the composition further comprises at least one surfactant.

46. The process according to claim 1, wherein the composition further comprises at least one additive chosen from dyestuffs, antioxidants, fillers, pasty fatty substances, preserving agents, fragrances, neutralizers, thickeners, vitamins, and plasticizers.

47. The process according to claim 1, wherein the composition does not comprise a UV-screening agent.

* * * * *

UNITED STATES PATENT AND TRADEMARK OFFICE
CERTIFICATE OF CORRECTION

PATENT NO. : 7,887,788 B2
APPLICATION NO. : 10/654907
DATED : February 15, 2011
INVENTOR(S) : Valerie De La Poterie Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1420 days.

Signed and Sealed this
Seventh Day of June, 2011

David J. Kappos
*Director of the United States Patent and Trademark Office*